US010627394B2

(12) United States Patent
Noordin et al.

(10) Patent No.: US 10,627,394 B2
(45) Date of Patent: Apr. 21, 2020

(54) STRONGYLOIDES STERCORALIS PROTEIN AND/OR CORRESPONDING DNA AND RNA SEQUENCES FOR APPLICATION IN DIAGNOSIS

(71) Applicant: Universiti Sains Malaysia, Pulau Pinang (MY)

(72) Inventors: Rahmah Binti Noordin, Pulau Pinang (MY); Norsyahida Binti Arifin, Pulau Pinang (MY)

(73) Assignee: Universiti Sains Malaysia, Pulau Pinang (MY)

( * ) Notice: Subject to any disclaimer, the term of this patent is extended or adjusted under 35 U.S.C. 154(b) by 10 days.

(21) Appl. No.: 15/778,430

(22) PCT Filed: Aug. 30, 2016

(86) PCT No.: PCT/MY2016/050053
§ 371 (c)(1),
(2) Date: May 23, 2018

(87) PCT Pub. No.: WO2017/091059
PCT Pub. Date: Jun. 1, 2017

(65) Prior Publication Data
US 2018/0356409 A1    Dec. 13, 2018

(30) Foreign Application Priority Data

Nov. 27, 2015 (MY) .............................. 2015002836

(51) Int. Cl.
*G01N 33/53* (2006.01)
*C07K 14/435* (2006.01)
*G01N 33/564* (2006.01)
*G01N 33/569* (2006.01)

(52) U.S. Cl.
CPC ....... *G01N 33/5308* (2013.01); *C07K 14/435* (2013.01); *G01N 33/564* (2013.01); *G01N 33/569* (2013.01); *C07K 2319/21* (2013.01); *C07K 2319/23* (2013.01); *G01N 2333/4353* (2013.01)

(58) Field of Classification Search
CPC .............. C07K 14/435; C07K 2319/21; C07K 2319/23; G01N 33/564; G01N 33/569; G01N 33/5308; G01N 2333/4353
See application file for complete search history.

(56) References Cited

FOREIGN PATENT DOCUMENTS

WO        2011/097216 A1     8/2011

OTHER PUBLICATIONS

GenBank Accession No. LL999076, Martin et al., (Strongyloides stercoralis genome assembly S_stercoralis_PV0001, scaffold SSTP_contig0000018, submitted Jul. 17, 2014). (Year: 2014).*

(Continued)

*Primary Examiner* — Jana A Hines
(74) *Attorney, Agent, or Firm* — Lathrop GPM LLP; Brian C. Trinque

(57) ABSTRACT

The present invention relates to methods of screening biological samples for the presence of *Strongyloides* spp. More particularly, the present invention relates to a sensitive and specific screening test for the presence of anti-*Strongyloides* spp antibodies, protein or nucleic acid in subjects using particular *Strongyloides* spp L3 stage antigens and nucleic acids encoding same which have diagnostic efficacy.

6 Claims, 12 Drawing Sheets
Specification includes a Sequence Listing.

(56) References Cited

OTHER PUBLICATIONS

Zueter, et al. (2014) "Detection of Strongyloides stercoralis infection among cancer patients in a major hospital in Kelantan, Malaysia," Singapore Medical Journal, vol. 55, pp. 367-371.
Anderson, et al. (2014) "Comparison of three immunoassays for detection of antibodies to Strongyloides stercoralis," Clinical and Vaccine Immunology, 2014, vol. 21, pp. 732-736.
International Search Report and Written Opinion of PCT/MY2016/050053 dated Oct. 31, 2016, 13 pp.

* cited by examiner

SEQ ID NO: 1

| | |
|---|---:|
| atggaggaca cagataattt aagtgttaag gatatctttc aaaagtatag aaatttaatc | 60 |
| cttaaagggg atggtaattt ttctgataaa caggaaatcc tagaaaagtc tattatagaa | 120 |
| atgaaaaaat taaaagataa ctttgatttg ggagatatta tatcattaaa tgaccaaata | 180 |
| gatgaaatat ctccatctga tcttgagatg ttccttctac catacttaat agggacagct | 240 |
| tattataatg ttaaagctac ggatcctaaa aaaaggatgg atgtattgtt gaatgttaag | 300 |
| atttatatgc aagagtatct tgaaaattta cacctctatt atatcattga ttttgtctta | 360 |
| ccatggctta aagataaaga agagtcatct agtgggcctt ctatatcaaa agatgacaaa | 420 |
| ttaactccat ccgaaaggag ggaaagaata cttaaaagac atcaaatgta taaaaatttt | 480 |
| gaagaaaagt tgttggagta tgaaaatgaa gcctcaacgg ctggtggttt ggatgatata | 540 |
| acacaaagaa attatgtcct agcaaagtta agaacttatg ctcttaaggc aatgatggat | 600 |
| ctcgagaaga ttggggagga acttggcata ttagagtata tgttaaaaat aaaacaaggt | 660 |
| gaagttgttg aggagaaaca taaacctcca ccaaaaatga caacttatcg tattgtaagg | 720 |
| aatgaggaac aaaaaaagtc tttggaatgg gttataaaaa tattccaaca cttactgtgg | 780 |
| atgagtggta tcgtgaaatg gatacaaaag gacattttaa tattaaacag gacgccggag | 840 |
| cacagcccaa tacctcaaat aatggaggag acgatgatga tgatgataat ttag | 894 |

FIGURE 2A

SEQ ID NO: 2

Met Glu Asp Thr Asp Asn Leu Ser Val Lys Asp Ile Phe Gln Lys Tyr
1               5                       10                      15

Arg Asn Leu Ile Leu Lys Gly Asp Gly Asn Phe Ser Asp Lys Gln Glu
                20              25                  30

Ile Leu Glu Lys Ser Ile Ile Glu Met Lys Lys Leu Lys Asp Asn Phe
            35              40                  45

Asp Leu Gly Asp Ile Ile Ser Leu Asn Asp Gln Ile Asp Glu Ile Ser
        50              55                  60

Pro Ser Asp Leu Glu Met Phe Leu Leu Pro Tyr Leu Ile Gly Thr Ala
65              70                      75                      80

Tyr Tyr Asn Val Lys Ala Thr Asp Pro Lys Lys Arg Met Asp Val Leu
                85                  90                  95

Leu Asn Val Lys Ile Tyr Met Gln Glu Tyr Leu Glu Asn Leu His Leu
                100             105                 110

Tyr Tyr Ile Ile Asp Phe Val Leu Pro Trp Leu Lys Asp Lys Glu Glu
            115             120                 125

Ser Ser Ser Gly Pro Ser Ile Ser Lys Asp Asp Lys Leu Thr Pro Ser
    130             135                 140

Glu Arg Arg Glu Arg Ile Leu Lys Arg His Gln Met Tyr Lys Asn Phe
145             150                 155                     160

Glu Glu Lys Leu Leu Glu Tyr Glu Asn Glu Ala Ser Thr Ala Gly Gly
                165             170                 175

Leu Asp Asp Ile Thr Gln Arg Asn Tyr Val Leu Ala Lys Leu Arg Thr
            180             185                 190

Tyr Ala Leu Lys Ala Met Met Asp Leu Glu Lys Ile Gly Glu Glu Leu
    195             200             205

Gly Ile Leu Glu Tyr Met Leu Lys Ile Lys Gln Gly Glu Val Val Glu
    210             215             220

Glu Lys His Lys Pro Pro Pro Lys Met Thr Thr Tyr Arg Ile Val Arg
225             230             235                         240

Asn Glu Glu Gln Lys Lys Ser Leu Glu Trp Val Ile Lys Ile Phe Gln
            245                 250             255

His Leu Leu Trp Met Ser Gly Ile Val Lys Trp Ile Gln Lys Asp Ile
            260             265                 270

Leu Ile Leu Asn Arg Thr Pro Glu His Ser Pro Ile Pro Gln Ile Met
        275             280             285

Glu Glu Thr Met Met Met Met Ile Ile
290                 295

FIGURE 2B

SEQ ID NO: 3

```
atatttctat atacttctca gctgaagtgt aattgttttt cagttttct actaacaatt   60 cacccaccaa ctaaccagtt tccactctaa tcttctaatg atgaatcgtt ctattctttt  120
ggtgctcttt gtttcattaa ttgctatggt ttcttgcaag agtctagcct cctactctga  180
taacggacca ctaggttcta tgttaagagc cgatgaatct actgacagtc ttggtgatgc  240
agtatctggt tctaccacct ctacaacaac acaagctcct tctactacca cttcagagtc  300
tttggaatct acttcgactt ctagtagttc ctcagaaaat ccaccttcag gtgccacggc  360
agctgccgct actatggata ttacttctac taccgccccc gacgagacta ctactaccac  420
agctccagcc gttgccactg aaactactac tactactact cctgctgtta caactacaac  480
agcaccaact gaagcaccaa ctcctgtcag taaggaagct accacaaccg aatcttcctc  540
tccagcaggt caggatgttt cctcaaccac agtcgagtca tcatcctccg ttccagagag  600
gagatcaaca tccagtgaac cctcagaaac gacaacatca ccaggagaaa tttcaacatc  660
tactggagct ggtaacacaa caacacctga accttctgct ggaagtgtta atggtgttca  720
atttaaagct atattgattt ctattatatc attatttgta tttttaattt gattgtagat  780
aatatatgtg gaaggataat ttactatttt aaataaaa                           818
```

FIGURE 3A

SEQ ID NO: 4:

| | | | | | | | | | | | | | | |
|---|---|---|---|---|---|---|---|---|---|---|---|---|---|---|
| Met 1 | Met | Asn | Arg | Ser 5 | Ile | Leu | Leu | Val | Leu 10 | Phe | Val | Ser | Leu | Ile 15 | Ala |
| Met | Val | Ser | Cys 20 | Lys | Ser | Leu | Ala | Ser 25 | Tyr | Ser | Asp | Asn | Gly 30 | Pro | Leu |
| Gly | Ser | Met 35 | Leu | Arg | Ala | Asp | Glu 40 | Ser | Thr | Asp | Ser | Leu 45 | Gly | Asp | Ala |
| Val | Ser 50 | Gly | Ser | Thr | Thr | Ser 55 | Thr | Thr | Thr | Gln | Ala 60 | Pro | Ser | Thr | Thr |
| Thr 65 | Ser | Glu | Ser | Leu | Glu 70 | Ser | Thr | Ser | Thr | Ser 75 | Ser | Ser | Ser | Ser | Glu 80 |
| Asn | Pro | Pro | Ser | Gly 85 | Ala | Thr | Ala | Ala | Ala 90 | Ala | Thr | Met | Asp | Ile 95 | Thr |
| Ser | Thr | Thr | Ala 100 | Pro | Asp | Glu | Thr | Thr 105 | Thr | Thr | Thr | Ala | Pro 110 | Ala | Val |
| Ala | Thr | Glu 115 | Thr | Thr | Thr | Thr | Thr 120 | Thr | Pro | Ala | Val | Thr 125 | Thr | Thr | Thr |
| Ala | Pro 130 | Thr | Glu | Ala | Pro | Thr 135 | Pro | Val | Ser | Lys | Glu 140 | Ala | Thr | Thr | Thr |
| Glu 145 | Ser | Ser | Ser | Pro | Ala 150 | Gly | Gln | Asp | Val | Ser 155 | Ser | Thr | Thr | Val | Glu 160 |
| Ser | Ser | Ser | Ser | Val 165 | Pro | Glu | Arg | Arg | Ser 170 | Thr | Ser | Ser | Glu | Pro 175 | Ser |
| Glu | Thr | Thr | Thr 180 | Ser | Pro | Gly | Glu | Ile 185 | Ser | Thr | Ser | Thr | Gly 190 | Ala | Gly |
| Asn | Thr | Thr 195 | Thr | Pro | Glu | Pro | Ser 200 | Ala | Gly | Ser | Val | Asn 205 | Gly | Val | Gln |
| Phe | Lys 210 | Ala | Ile | Leu | Ile | Ser 215 | Ile | Ile | Ser | Leu | Phe 220 | Val | Phe | Leu | Ile |

FIGURE 3B

Alignment of the DNA sequence of clone SsIa with GenBank

```
SEQ ID NO: 1      TTA-AGATTTATATGCAAGAGTATCTTGAAAATTTACACCTCTATTATATCATTGATTTT   354
                  ||| ||||||||||||||||||||||||||||||||||||||||||||||||||||||||
Sbjct   154435    TTATAGATTTATATGCAAGAGTATCTTGAAAATTTACACCTCTATTATATCATTGATTTT   154494

SEQ ID NO: 1      GTCTTACCATGGCTTAAAGATAAAGAAGAGTCATCTAGTGGGCCTTCTATATCAAAAGAT   414
                  ||||||||||||||||||||||||||||||||||||||||||||||||||||||||||||
Sbjct   154495    GTCTTACCATGGCTTAAAGATAAAGAAGAGTCATCTAGTGGGCCTTCTATATCAAAAGAT   154554

SEQ ID NO: 1      GACAAATTAACTCCATCCGAAAGGAGGGAAAGAATACTTAAAAGACATCAAATGTATAAA   474
                  ||||||||||||||||||||||||||||||||||||||||||||||||||||||||||||
Sbjct   154555    GACAAATTAACTCCATCCGAAAGGAGGGAAAGAATACTTAAAAGACATCAAATGTATAAA   154614

SEQ ID NO: 1      AATTTTGAAGAAAAGTTGTTGGAGTATGAAAATGAAGCCTCAACGGCTGGTGGTTTGGAT   534
                  ||||||||||||||||||||||||||||||||||||||||||||||||||||||||||||
Sbjct   154615    AATTTTGAAGAAAAGTTGTTGGAGTATGAAAATGAAGCCTCAACGGCTGGTGGTTTGGAT   154674

SEQ ID NO: 1      GATATAACACAAAGAAATTATGTCCTAGCAAAGTTAAGAACTTATGCTCTTAAGGCAATG   594
                  ||||||||||||||||||||||||||||||||||||||||||||||||||||||||||||
Sbjct   154675    GATATAACACAAAGAAATTATGTCCTAGCAAAGTTAAGAACTTATGCTCTTAAGGCAATG   154734

SEQ ID NO: 1      ATGGATCTCGAGAAGATTGGGGAGGAACTTGGCATATTAGAGTATATGTTAAAAATAAAA   654
                  ||||||||||||||||||||||||||||||||||||||||||||||||||||||||||||
Sbjct   154735    ATGGATCTCGAGAAGATTGGGGAGGAACTTGGCATATTAGAGTATATGTTAAAAATAAAA   154794

SEQ ID NO: 1      CAAGGTGAAGTTGTTGAGGAGAAACATAAACCTCCACCAAAAATGACAACTTATCGTATT   714
                  ||||||||||||||||||||||||||||||||||||||||||||||||||||||||||||
Sbjct   154795    CAAGGTGAAGTTGTTGAGGAGAAACATAAACCTCCACCAAAAATGACAACTTATCGTATT   154854

SEQ ID NO: 1      GTAAGGAATGAGGAAC-aaaaaaaGTCTTTGGAATGGGTTATAAAAATATTCCAACACTT   773
                  ||||||||||||||||         |||||||||||||||||||||||||||||||||||
Sbjct   154855    GTAAGGAATGAGGAACAAAAAAAAGTCTTTGGAATGGGTTATAAAAATATTCCAACACTT   154914

SEQ ID NO: 1      ACTGTGGATGAGTGGTATCGTGAAATGGATACAAAAGGACATTTTAATATTAAACAGGAC   833
                  ||||| ||||||||||||||||||||||||||||||||||||||||||||||||||||||
Sbjct   154915    ACTGTTGATGAGTGGTATCGTGAAATGGATACAAAAGGACATTTTAATATTAAACAGGAC   154974

SEQ ID NO: 1      GCCGGAGCACAGCCCAATACCTCAAATAATGGAGGAGACGATGATGATGATGATAATTTA   893
                  ||||||||||||||||||||||||||||||||||||||||||||||||||||||||||||
Sbjct   154975    GCCGGAGCACAGCCCAATACCTCAAATAATGGAGGAGACGATGATGATGATGATAATTTA   155034

SEQ ID NO: 1      G   894
                  |
Sbjct   155035    G   155035
```

FIGURE 4

Alignment of the protein sequence of rSsIa with GenBank

```
SEQ ID NO: 2   MEDTDNLSVKDIFQKYRNLILKGDGNFSDKQEILEKSIIEMKKLKDNFDLGDIISLNDQI   60
               ME T + SV+++FQKYR+LILKGDG+FSDKQ+ LE SI+EMKKLKDN ++ DIISLNDQI
S ratti        MEKTGDFSVREVFQKYRDLILKGDGSFSDKQDFLENSIVEMKKLKDNLEIEDIISLNDQI   60

SEQ ID NO: 2   DEISPSDLEMFLLPYLIGTAYYNVKATDPKKRMDVLLNVKIYMQEYLENLHLYYIIDFVL   120
               DEIS ++LEMFLLPYLIGTAYYN++ATDPKKRMDVLLNV+ Y++EYLE+L +YYI F L
S ratti        DEISATNLEMFLLPYLIGTAYYNIRATDPKKRMDVLLNVRTYLREYLEHLRIYYIIGFSL   120

SEQ ID NO: 2   PWLKDKEES-SSGPSISKDDKLTPSERRERILKRHQMYKNFEEKLLEYENEASTAGGLDD   179
               PWL+DKEE  S    SISK+DKLTPSERRERILKRHQMYKNFEEKLLE+E+EAST+GGLD+
S ratti        PWLRDKEEEPSDSSSISKEDKLTPSERRERILKRHQMYKNFEEKLLEFEHEASTSGGLDE   180

SEQ ID NO: 2   ITQRNYVLAKLRTYALKAMMDLEKIGEELGILEYMLKIKQGEVVEEKHKPPPKMTTYRIV   239
               ++QRN++LAKLRT+A KAMMDLEK+ EELGILE+MLK+K+GE+ EEK KPP K++TYRIV
S ratti        VSQRNFILAKLRTFAFKAMMDLEKVDEELGILEHMLKLKRGEISEEKPKPPVKLSTYRIV   240

SEQ ID NO: 2   RNEEQKK   246
               RNEEQKK
S ratti        RNEEQKK   247
```

FIGURE 5

Alignment of the DNA sequence of clone Ss3a with GenBank

```
SEQ ID NO: 3    ATATTTCTATATACTTCTCAGCTGAAGTGTAATTGTTTTTCAGTTTTTCTACTAACAATT   60
                ||||||||||||||||||||||||||||||||||||||||||||||||||||||||||||
Sbjct   938039  ATATTTCTATATACTTCTCAGCTGAAGTGTAATTGTTTTTCAGTTTTTCTACTAACAATT   937980

SEQ ID NO: 3    CACCCACCAACTAACCAGTTTCCACTCTAATCTTCTAATGATGAATCGTTCTATTCTTTT   120
                ||||||||||||||||||||||||||||||||||||||||||||||||||||||||||||
Sbjct   937979  CACCCACCAACTAACCAGTTTCCACTCTAATCTTCTAATGATGAATCGTTCTATTCTTTT   937920

SEQ ID NO: 3    GGTGCTCTTTGTTTCATTAATTGCTATGGTTTCTTGCAAGAGTCTAGCCTCCTACTCTGA   180
                ||||||||||||||||||||||||||||||||||||||||||||||||||||||||||||
Sbjct   937919  GGTGCTCTTTGTTTCATTAATTGCTATGGTTTCTTGCAAGAGTCTAGCCTCCTACTCTGA   937860

SEQ ID NO: 3    TAACGGACCACTAGGTTCTATGTTAAGAGCCGATGAATCTACTGACAGTCTTGGTGATGC   240
                ||||||||||||||||||||||||||||||||||||||||||||||||||||||||||||
Sbjct   937859  TAACGGACCACTAGGTTCTATGTTAAGAGCCGATGAATCTACTGACAGTCTTGGTGATGC   937800

SEQ ID NO: 3    AGTATCTGGTTCTACCACCTCTACAACAACACAAGCTCCTTCTACTACCACTTCAGAGTC   300
                ||||||||||||||||||||||||||||||||||||||||||||||||||||||||||||
Sbjct   937799  AGTATCTGGTTCTACCACCTCTACAACAACACAAGCTCCTTCTACTACCACTTCAGAGTC   937740

SEQ ID NO: 3    TTTGGAATCTACTTCGACTTCTAGTAGTTCCTCAGAAAATCCACCTTCAGGTGCCACGGC   360
                ||||||||||||||||||||||||||||||||||||||||||||||||||||||||||||
Sbjct   937739  TTTGGAATCTACTTCGACTTCTAGTAGTTCCTCAGAAAATCCACCTTCAGGTGCCACGGC   937680

SEQ ID NO: 3    AGCTGCCGCTACTATGGATATTACTTCTACTACCGCCCCCGACGAGACTACTACTACCAC   420
                ||||||||||||||||||||||||||||||||||||||||||||||||||||||||||||
Sbjct   937679  AGCTGCCGCTACTATGGATATTACTTCTACTACCGCCCCCGACGAGACTACTACTACCAC   937620

SEQ ID NO: 3    AGCTCCAGCCGTTGCCACTGAAactactactactact CCTGCTGTTACAACTACAAC   480
                ||||||||||||||||||||||||||||||||||||||||||||||||||||||||||||
Sbjct   937619  AGCTCCAGCCGTTGCCACTGAAACTACTACTACTACTACTCCTGCTGTTACAACTACAAC   937560

SEQ ID NO: 3    AGCACCAACTGAAGCACCAACTCCTGTCAGTAAGGAAGCTACCACAACCGAATCTTCCTC   540
                ||||||||||||||||||||||||||||||||||||||||||||||||||||||||||||
Sbjct   937559  AGCACCAACTGAAGCACCAACTCCTGTCAGTAAGGAAGCTACCACAACCGAATCTTCCTC   937500

SEQ ID NO: 3    TCCAGCAGGTCAGGATGTTTCCTCAACCACAGTCGAGTCATCATCCTCCGTTCCAGAGAG   600
                ||||||||||||||||||||||||||||||||||||||||||||||||||||||||||||
Sbjct   937499  TCCAGCAGGTCAGGATGTTTCCTCAACCACAGTCGAGTCATCATCCTCCGTTCCAGAGAG   937440

SEQ ID NO: 3    GAGATCAACATCCAGTGAACCCTCAGAAACGACAACATCACCAGGAGAAATTTCAACATC   660
                ||||||||||||||||||||||||||||||||||||||||||||||||||||||||||||
Sbjct   937439  GAGATCAACATCCAGTGAACCCTCAGAAACGACAACATCACCAGGAGAAATTTCAACATC   937380

SEQ ID NO: 3    TACTGGAGCTGGTAACACAACAACACCTGAACCTTCTGCTGGAAGTGTTAATGGTGTTCA   720
                ||||||||||||||||||||||||||||||||||||||||||||||||||||||||||||
Sbjct   937379  TACTGGAGCTGGTAACACAACAACACCTGAACCTTCTGCTGGAAGTGTTAATGGTGTTCA   937320

SEQ ID NO: 3    ATTTAAAGCTATATTGATTTCTATTATATCATTATTTGAATTTTTAATTTGATTGTAGAT   780
                ||||||||||||||||||||||||||||||||||||| ||||||||||||||||||||||
Sbjct   937319  ATTTAAAGCTATATTGATTTCTATTATATCATTATTTGTATTTTTAATTTGATTGTAGAT   937260

SEQ ID NO: 3    AATATATGTGGAAGGATAATTTACTATTTTAAATaaaaa   819
                |||||||||||||||||||||||||||||||||||||||
Sbjct   937259  AATATATGTGGAAGGATAATTTACTATTTTAAATAAAAA   937221
```

FIGURE 6

Alignment of the protein sequence of rSs3a with GenBank

```
SEQ ID NO: 4   ESSSPAGQDVSSTTVESSSSVPERRSTSSEPSETTTSPGEISTSTGAGNTTTPEPSAGSV   204
               ES+SP+ QD+SSTT  SSSS P+RRSTSSE ETTT+   STSTG   TTT EPSAGS
S ratti        ESTSPSSQDLSSTTTASSSSAPQRRSTSSESPETTTAAPGSSTSTGTDGTTTAEPSAGSA   202

SEQ ID NO: 4   NGVQFKAILISIIS-LFVFLI   224
               + +QFK ILISI+S LFVFL
S ratti        SDIQFKTILISILSFLFVFLF   223
```

FIGURE 7

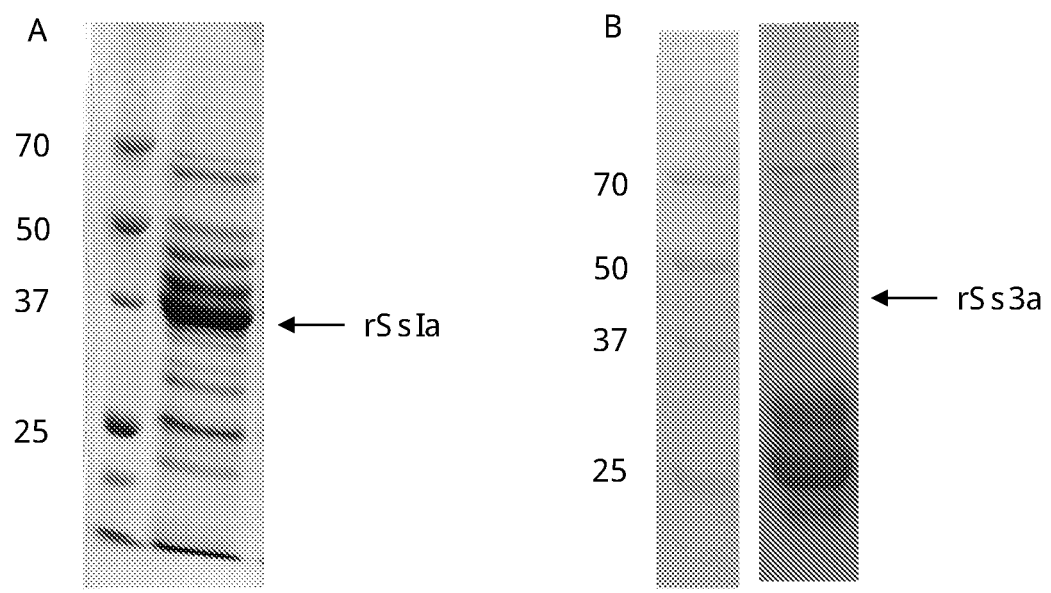
FIGURE 8A-B

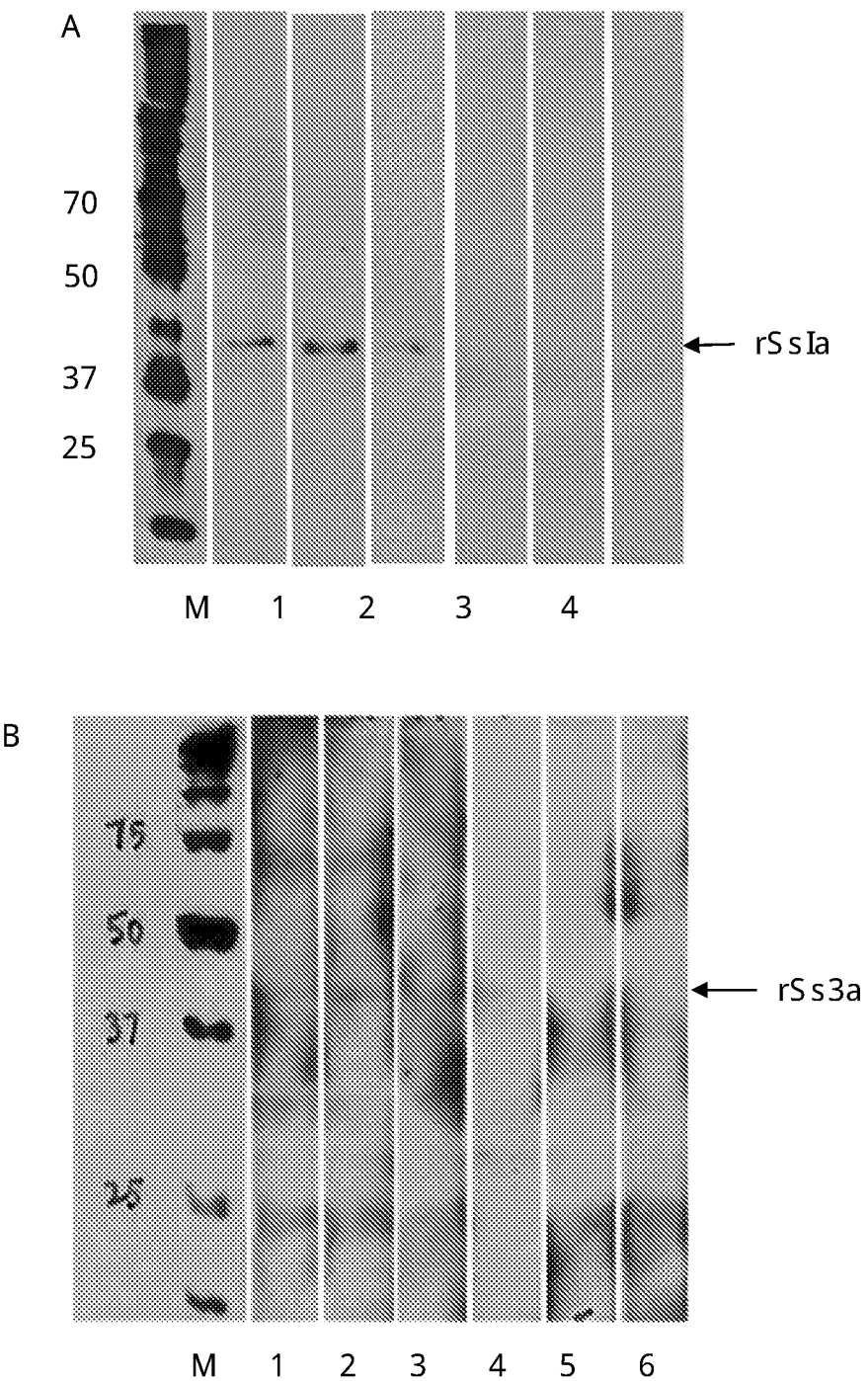
FIGURE 9A-B

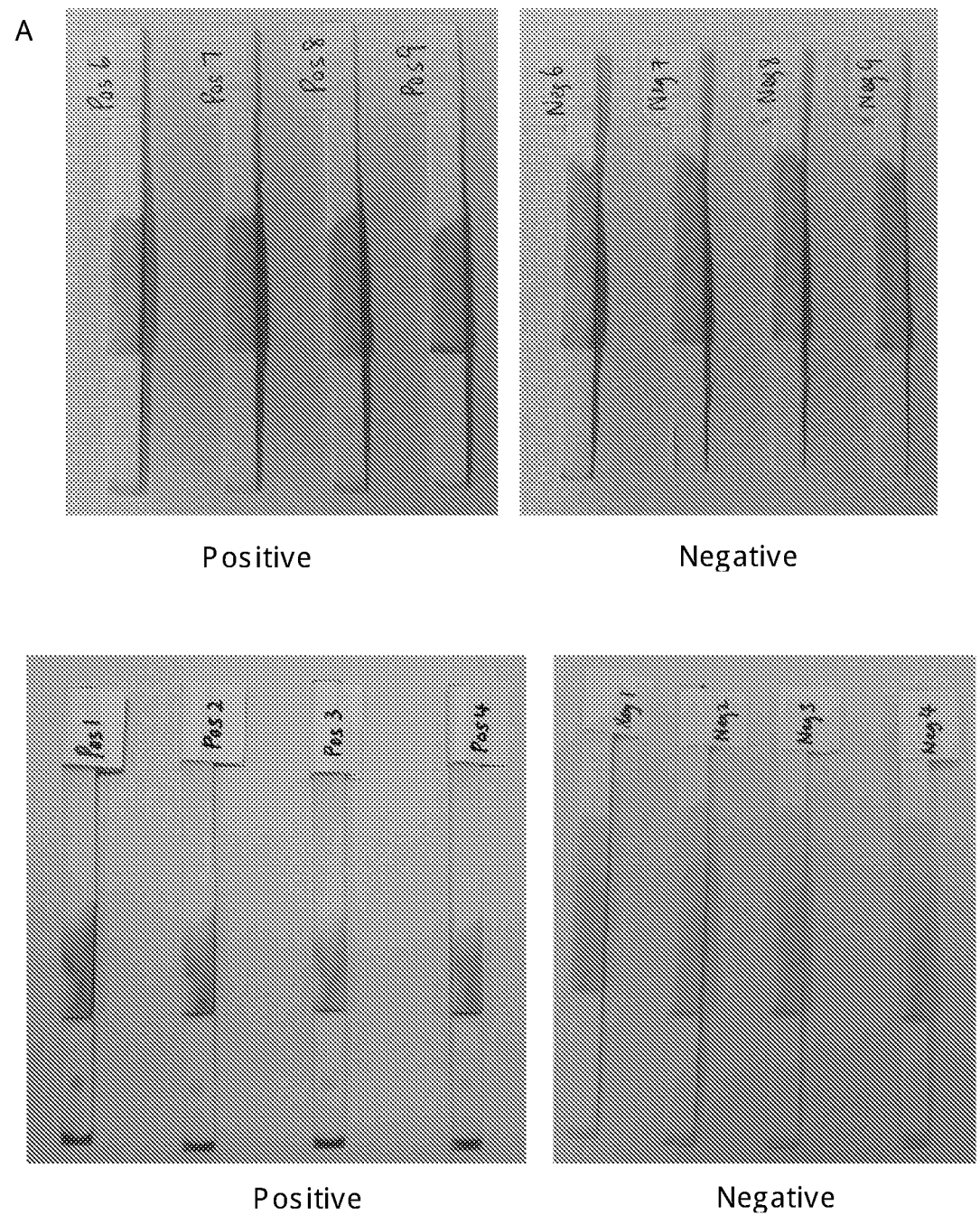
FIGURE 10A-B

STRONGYLOIDES STERCORALIS PROTEIN AND/OR CORRESPONDING DNA AND RNA SEQUENCES FOR APPLICATION IN DIAGNOSIS

CROSS-REFERENCE TO RELATED APPLICATIONS

This application is a 35 U.S.C. § 371 filing of International Application No. PCT/MY2016/050053, filed on Aug. 30, 2016, which claims priority to Malaysian patent application number PI 2015002836, filed Nov. 27, 2015. The entire contents of these applications are incorporated by reference herein, in their entirety.

FIELD OF THE INVENTION

The present invention relates to methods of screening biological samples for the presence of *Strongyloides* spp. More particularly, the present invention relates to a sensitive and specific screening test for the presence of anti-*Strongyloides* spp antibodies, protein or nucleic acid in subjects using particular *Strongyloides* spp L3 stage antigens and nucleic acids encoding same which have diagnostic efficacy.

BACKGROUND

Strongyloidiasis is considered to be one of the most neglected tropical diseases, mainly due to the poor sensitivity of the available diagnostic tests and lack of precise data on the epidemiology and seroprevalence of the disease especially in the endemic countries. The disease is mainly caused by a pathogenic species *Strongyloides stercoralis* that infects humans percutaneously. This parasite has a world-wide distribution and it is more prevalent in tropical and subtropical regions when poor sanitary conditions exist. The global prevalence of the disease is underestimated, however about 100-350 million people are estimated to be infected worldwide, mostly among the poorest residing in the least-developed countries (Requena-Mendez A., et al., Curr Trop Med Rep, 1: 207-215 (2014)).

Although *Strongyloides stercoralis* is the main species infecting humans, there are two other species that infect humans, namely *Strongyloides fuelleborni* and *Strongyloides kellyi*, which are seen only in a few places in the world. The present application shall refer to this group as *Strongyloides* spp, including but not limited to the above species, and preferably *Strongyloides stercoralis*.

The health consequences of *S. stercoralis* infections range from asymptomatic light infections to chronic symptomatic strongyloidiasis involving anything from mild gastrointestinal morbidity to severe life-threatening conditions (Olsen A., et al., Trans. R. Soc. Trop. Med. Hyg. 103: 967-972 (2009)). In immunocompetent persons, the infection usually remains undiagnosed and the parasite may persist in the human host for decades through the autoinfection cycle of the parasite. Meanwhile, in immunosuppressive conditions, autoinfection may dominate and become overwhelming, with parasites at different stages of development invading virtually every host organ and tissue, resulting in development of hyperinfection and disseminated strongyloidiasis with a mortality rate as high as 87% (Siddiqui A A., and Berk S L., Travel Medicine, 33: 1040-1047 (2001)). As in the United States, almost all deaths due to helminths result from *S. stercoralis* hyperinfection (Muennig P., et al., N Engl J Med, 340: 773-779 (1999)).

Humans are exposed to *S. stercoralis* infection through direct contact with contaminated soil during agricultural, domestic and recreational activities. There is no gold standard test to rule out the infection, however the mainstay of diagnostic testing relies on the demonstration of larval stages in faecal specimens (Ramanathan R., et al., The Journal of Infectious Diseases, 198: 44-451 (2008)). To date, there are three test kits available (i) :Bordier-ELISA ˇ(Bordier Affinity products SA, Switzerland); (ii) :SciMedx *Strongyloides* serology microwell ELISA ˇ(SciMedx Corporation, Denville, N.J., USA); and (iii) :InBios Strongy Detect IgG ELISA ˇ(InBios International, Inc., Seattle, Wash., USA). The first two tests are based on a one-step sandwich format immunoassay for qualitative detection of IgG-antibodies to *Strongyloides* antigen. The kit by InBios International is a one-step sandwich format immunoassay for detection of IgG-antibodies to the *Strongyloides* recombinant NIE antigen (Anderson N W., et al., Clin. Vaccine Immunol., 21: 732-736 (2014)). However this kit is still in development stage, as stated in the companyš website. One major drawback of these three tests is the need for an enzyme immunoassay analyzer (EIA) to measure the optical density of the reaction samples, which is impractical for point-of care in many settings.

The application of immunological screening of a cDNA library in identifying species specific genes has been established by many researchers over the past 30 years.

With regard to detection of strongyloidiasis, studies related to the construction of a cDNA library for identification of genes expressed in the L3 stage were undertaken by Ravi and co-workers (Ravi V., et al., Mol. Biochem. Parasitol., 125: 73-81 (2002)). They found a promising candidate gene that encodes for a 31 kDa NIE-recombinant protein. The recombinant protein was first incorporated into an assay which uses a luciferase immunoprecipitation system (LIPS) (Requena-M¶indez A., et al., PLoS Negl. Trop. Dis., 7: e2002 (2013); (Ramanathan R., et al., The Journal of Infectious Diseases, 198: 44-451 (2008)). LIPS is a modified ELISA in which serum containing antigen specific antibodies can be identified by measuring light production and requires the use of a vacuum manifold, a microplate luminometer for determining the luminescence and a mathematical analysis to obtain a read-out. As mentioned above, InBios International Inc are developing an IgG-ELISA using the NIE recombinant protein.

Currently there are no simple, rapid and convenient diagnostic methods suitable for use in low-resource countries where strongyloidiasis is endemic that avoid the requirement for sophisticated equipment.

In light of the disadvantages of current methods of detecting strongyloidiasis, there is a need to develop new markers and improved tests for the disease that have high selectivity and specificity.

SUMMARY OF THE INVENTION

A *Strongyloides stercoralis* cDNA library was screened and clones encoding L3 larvae stage antigens were identified for specific detection of strongyloidiasis. Recombinant proteins from two such candidates show high diagnostic sensitivity and specificity using western blots and were used to develop lateral flow (immunochromatography) dipstick dot tests.

Accordingly, in a first aspect, the present invention provides the use of an isolated or recombinant *Strongyloides* spp protein comprising the amino acid sequence shown in SEQ ID NO: 2 or SEQ ID NO: 4, or a fragment or variant thereof, to detect *Strongyloides* spp in an isolated biological sample.

In a preferred embodiment of the invention the *Strongyloides* spp protein or fragment or variant thereof is encoded by an isolated or recombinant nucleic acid molecule comprising the nucleic acid sequence shown in SEQ ID NO: 1 or SEQ ID NO: 3 or a fragment thereof.

In a preferred embodiment the invention provides the use of an isolated or recombinant *Strongyloides* spp nucleic acid comprising the nucleic acid sequence shown in SEQ ID NO: 1 or SEQ ID NO: 3, or a fragment thereof, to detect *Strongyloides* spp nucleic acid in an isolated biological sample.

In another preferred embodiment the presence of *Strongyloides* spp is indicated by specific and selective binding of the isolated or recombinant *Strongyloides* spp protein, comprising the amino acid sequence shown in SEQ ID NO: 2 or SEQ ID NO: 4, or a fragment or variant thereof, to *Strongyloides* spp-specific antibodies present in the isolated biological sample.

The biological sample may be from an animal, including a human subject

According to another aspect of the invention, there is provided a method of detecting *Strongyloides* spp in a biological sample, comprising the steps of:
a) contacting the biological sample with an antigen, wherein the antigen is an isolated or recombinant *Strongyloides* spp protein, comprising the amino acid sequence shown in SEQ ID NO: 2 or SEQ ID NO: 4 or an antigenic fragment or variant thereof; and
b) detecting specific and selective antigen-antibody binding, wherein the binding indicates the presence of *Strongyloides* spp-specific antibodies present in the biological sample.

In a preferred embodiment of the method of the invention, the antigen-antibody binding is detected using immunoassay. The immunoassay may include various formats, for example ELISA, Western blot, flow-through (vertical flow) test or lateral flow assay.

According to another aspect of the invention, there is provided a method of detecting *Strongyloides* spp in a biological sample, comprising the steps of:
a) providing at least one biological sample;
b) contacting the at least one biological sample with an antibody directed against at least one *Strongyloides* protein;
c) detecting the presence of *Strongyloides* protein in the biological sample, wherein the detection of the *Strongyloides* protein comprising the amino acid sequence shown in SEQ ID NO: 2 or SEQ ID NO: 4 or fragment thereof in the biological sample constitutes detection of *Strongyloides*.

In another preferred embodiment of the method of the invention, the *Strongyloides* protein is detected with an antibody that specifically and selectively binds the protein, and the nucleic acid is detected using nucleic acid amplification.

In another preferred embodiment of the method of the invention, the *Strongyloides* protein is detected using immunoassay.

According to another aspect of the invention, there is provided a method of detecting whether a subject has strongyloidiasis, comprising the steps;
a) contacting a test sample from the subject with an antigen, wherein the antigen is an isolated or recombinant *Strongyloides* protein or a fragment thereof, and detecting specific and selective antibody-antigen binding, wherein the binding indicates the presence of strongyloidiasis in the subject; or
b) detecting the presence of *Strongyloides* protein, or nucleic acid molecule encoding same, in a test sample from the subject, wherein the detection of the *Strongyloides* protein or nucleic acid molecule in the test sample indicates the presence of strongyloidiasis.

According to another aspect of the invention, there is provided an expression construct comprising a nucleic acid comprising the sequence shown in SEQ ID NO: 1 or SEQ ID NO: 3 or antigen-encoding fragment thereof.

According to another aspect of the invention, there is provided a kit for screening a biological sample for the presence of *Strongyloides*-specific antibody and/or *Strongyloides* antigen, comprising:
a) an isolated or recombinant *Strongyloides* protein, or a fragment thereof according to any aspect of the invention, capable of binding to *Strongyloides*-specific antibody present in the biological sample; and/or
b) an isolated or recombinant *Strongyloides* protein-specific antibody according to any aspect of the invention, capable of binding to *Strongyloides* protein present in the biological sample.

BRIEF DESCRIPTION OF THE FIGURES

FIG. 2A: The 894 nucleotide sequence of the insert of the phage clone Ss1a of *Strongyloides stercoralis* L3 larvae stage is represented by SEQ ID NO: 1. The nucleotides encoding the predicted protein sequence are underlined.

FIG. 2B: The predicted 297 amino acid sequence encoded by the insert of the phage clone Ss1a of *Strongyloides stercoralis* L3 larvae stage is represented by SEQ ID NO: 2.

FIG. 3A: The 818 nucleotide sequence of the insert of the phage clone Ss3a of *Strongyloides stercoralis* L3 larvae stage is represented by SEQ ID NO: 3. The nucleotides encoding the predicted protein sequence are underlined.

FIG. 3B: The predicted 224 amino acid sequence encoded by the insert of the phage clone Ss3a of *Strongyloides stercoralis* L3 larvae stage is represented by SEQ ID NO: 4.

FIG. 4: Alignment of the DNA sequence of the insert of clone Ss1a (SEQ ID NO: 1) with GenBank database shows a high level of identity (99%) with a region of *Strongyloides stercoralis* genome assembly S_stercoralis_PV0001, scaffold SSTP_contig0000018; Sequence ID: emb LL999076.1. There are two gaps in the clone sequence; at 299 and 731; and a substitution of T/G at position 779.

FIG. 5: Blastp alignment of rSs1a clone predicted protein sequence (SEQ ID NO: 2) shows 76% identity and 91% homology with *Strongyloides ratti* Immunoglobulin-binding protein 1 (Accession emb CEF66010.1). There is one gap in the clone sequence at amino acid position 130.

FIG. 6: Alignment of the DNA sequence of the insert of clone Ss3a (SEQ ID NO: 3) with GenBank database shows a high level of identity (99%) with a reverse complementary region of *Strongyloides stercoralis* genome assembly S_stercoralis_PV0001, scaffold SSTP_scaffold0000002. Sequence ID: There is a substitution of T/A at position 759.

FIG. 7: Blastp alignment of rSs3a clone predicted protein sequence (SEQ ID NO: 4) shows 67% identity and 76% homology with *Strongyloides ratti* hypothetical protein SRAE_2000383300 (Accession emb CEF69183.1). There is one gap in the clone sequence at amino acid position 218 to maximise alignment.

FIG. 8A-B: SDS-PAGE profile of *E. coli*-expressed rSsIa protein A) and rSs3a protein B).

FIG. 9A-B: Western blot profiles of rSsIa antigen (A) and rSs3a antigen (B) probed with anti-*S. stercoralis* antibody-positive and negative human serum samples. Lane M: Low molecular weight marker; Lanes 1-3: Antibody-positive serum samples; Lanes 4-6: Antibody-negative serum samples.

FIG. 10A-B: Representative images of dot-dipstick tests using A) rSsIa and B) rSs3a and probed with positive and negative serum samples.

DETAILED DESCRIPTION

Definitions

Figure 1:
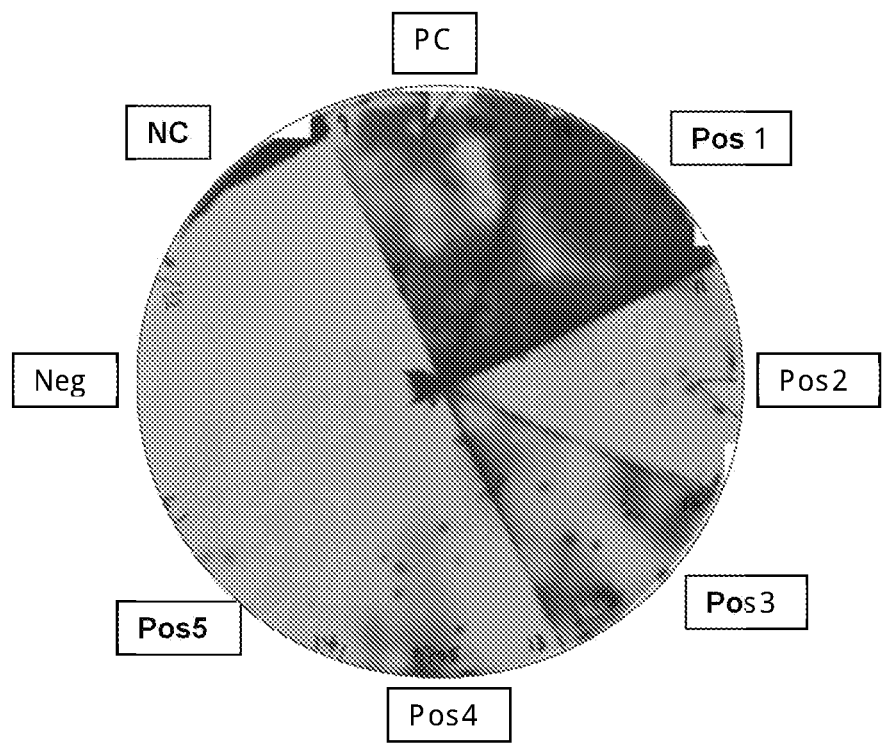
FIG. 1: Representative results of sensitivity and specificity evaluation of clone Ss3a by phage immunoblot. PC: positive control serum; NC: negative control serum; Pos: serum from patients with strongyloidiasis; Neg: serum from a healthy individual.
Figure 1:
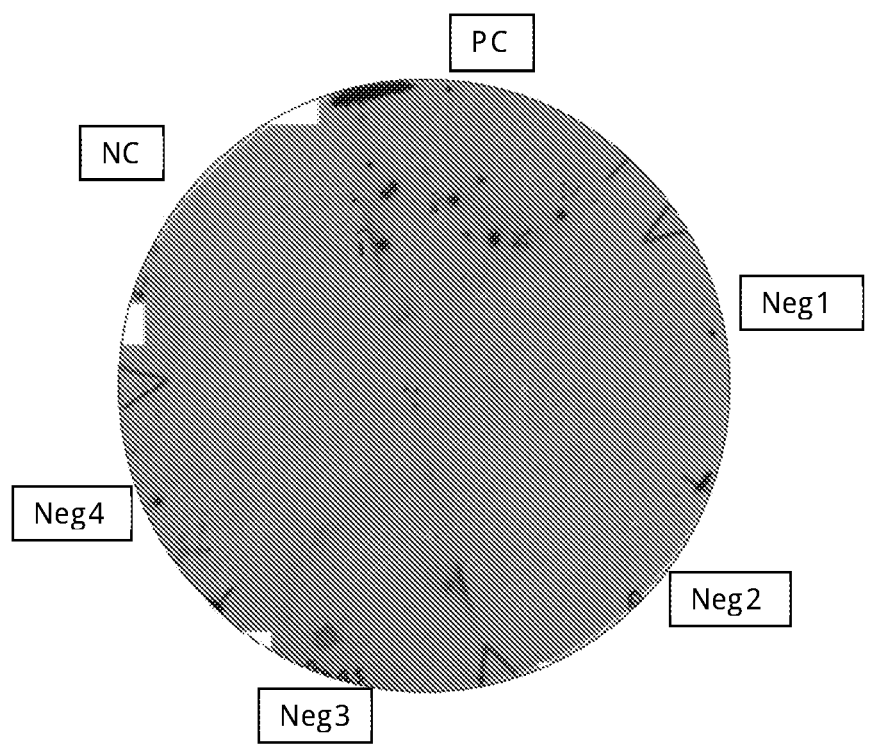

Certain terms employed in the specification, examples and appended claims are collected here for convenience.

The terms "amino acid" or "amino acid sequence," as used herein, refer to an oligopeptide, peptide, polypeptide, or protein sequence, or a fragment of any of these, and to naturally occurring or synthetic molecules. The term '*Strongyloides* protein sequence, as used herein, refers to an antigenic polypeptide used to identify and or generate *Strongyloides* protein-specific antibodies.

In this context "fragments" refers to a *Strongyloides* protein according to the invention which has been reduced in length by one or more amino acids and which retains antigenic activity sufficient to raise and or detect antibodies specific to *Strongyloides* Immunoglobulin-binding protein 1 or hypothetical protein SRAE. For example, the rSs1a antigen described in the present application is produced from the Ss1a DNA clone of SEQ ID NO: 1 and has the amino acid sequence defined in SEQ ID NO: 2, and the aligned sequence in FIG. 5 may be considered a fragment of the protein of SEQ ID NO: 2. It would be understood that the rSs1a antigen polypeptide could be further reduced in length (i.e. fragmented) and retain a *Strongyloides* Immunoglobulin-binding protein 1 epitope that binds to serum IgG from subjects with strongyloidiasis.

As used herein, the terms "specific binding" or "specifically binding" refer to that interaction between a protein or peptide and an agonist, an antibody, or an antagonist. The interaction is dependent upon the presence of a particular structure of the protein recognized by the binding molecule (i.e., the antigenic determinant or epitope). For example, if an antibody is specific for epitope "A," the presence of a polypeptide containing the epitope A, or the presence of free unlabeled A, in a reaction containing free labeled A and the antibody will reduce the amount of labeled A that binds to the antibody. In the context of the invention, specificity refers to the lack of reactivity of the *Strongyloides* protein of SEQ ID NO: 2 or 4, or an antigenic fragment thereof, with serum from healthy individuals or from patients with other infections. Thus if 9 serum samples are not reactive out of 10 healthy sera, the specificity of the antigen in the detection of anti-*Strongyloides* antibodies is 90%.

As used herein, the term "sensitive binding" or 'sensitivity_refers to the number of serum samples from *Strongyloides* infected individuals who are reactive with the *Strongyloides* protein of SEQ ID NO: 2 or 4, or antigenic fragments thereof. Thus if 8 serum samples are reactive out of 10 infected sera, the sensitivity of the antigen in the detection of anti-*Strongyloides* antibodies is 80%.

An antibody is any immunoglobulin, including antibodies and fragments thereof that bind to a specific epitope. The antibody according to the invention may be prepared against a polypeptide having the amino acid sequence of at least one of SEQ ID NOS: 2 or 4 or an antigenic fragment thereof. Such antibodies include, but are not limited to, isolated and/or recombinant polyclonal, monoclonal, chimeric, humanised, single chain, Fab, Fab˘, F(ab)˘ fragments and/or F(v) portions of the whole antibody.

The term :variant˘, as used in the context of the present invention is intended to describe variations to the amino acid sequence of the *Strongyloides* protein of SEQ ID NO: 2 or 4 that do not remove the antigenicity of the polypeptide in terms of eliciting antibodies which bind to the *Strongyloides* protein. Variants include conservative amino acid substitutions, and additions or deletions of amino acids that do not affect antigenicity. A variant may include a homologous sequence from a *Strongyloides* species other than *S. stercoralis*, such as *S. ratti*.

A "conservative amino acid substitution" as used herein is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, one or more amino acid residues in a *Strongyloides* protein comprising, essentially consisting of, or consisting of the amino acid sequence encoded by the nucleic acid sequence defined by SEQ ID NO: 1 or 3, or a fragment thereof, may be replaced with one or more other amino acid residues from the same side chain family without significantly reducing the antigenicity of the polypeptide or deviating significantly from the scope of the present invention.

The term "treatment", as used in the context of the invention refers to prophylactic, ameliorating, therapeutic or curative treatment.

The term "comprising" as used in the context of the invention refers to where the various components, ingredients, or steps, can be conjointly employed in practicing the present invention. Accordingly, the term "comprising" encompasses the more restrictive terms "consisting essentially of" and "consisting of". With the term 'consisting essentially of_it is understood that the epitope/antigen of the present invention 'substantially_comprises the indicated sequence as 'essential_element Additional sequences may be included at the 5˘ end and/or at the 3˘ end. Accordingly, a polypeptide 'consisting essentially of_sequence X will be novel in view of a known polypeptide accidentally comprising the sequence X. With the term 'consisting of_it is understood that the polypeptide, polynucleotide and/or antigen according to the invention corresponds to at least one of the indicated sequence (for example a specific sequence indicated with a SEQ ID Number or a homologous sequence or fragment thereof).

Accordingly, in a first aspect, the present invention provides the use of an isolated or recombinant *Strongyloides stercoralis* protein comprising the amino acid sequence shown in SEQ ID NO: 2 or SEQ ID NO: 4, or a fragment or variant thereof, to detect *Strongyloides* spp in an isolated biological sample.

In a preferred embodiment, the *Strongyloides* spp may be selected from the group comprising *Strongyloides stercoralis, Strongyloides fuelleborni* and *Strongyloides kellyi*.

In a preferred embodiment of the invention the *Strongyloides stercoralis* protein or fragment or variant thereof is encoded by an isolated or recombinant nucleic acid molecule comprising the nucleic acid sequence shown in SEQ ID NO: 1 or SEQ ID NO: 3, or a fragment thereof. The fragment thereof may comprise or consist of the nucleic acids of clones Ss1a and/or Ss3a represented by nucleotides 1-891 or 98-770, respectively. The skilled person would understand that these nucleic acids could be further reduced in length and still be capable of encoding an antigenic protein that could be used to detect anti-*Strongyloides* antibodies in, for example, an isolated biological sample. More particularly, the biological sample may be serum of an infected subject.

In another preferred embodiment the presence of *Strongyloides* is indicated by specific and selective binding of the isolated or recombinant *Strongyloides stercoralis* protein, comprising the amino acid sequence shown in SEQ ID NO: 2 or SEQ ID NO: 4, or antigenic fragment or variant thereof, to *Strongyloides stercoralis*-specific antibodies present in the isolated biological sample.

The biological sample may be from any source that may contain *Strongyloides*. More particularly the sample may be from an animal, preferably a mammal, more preferably a human subject.

According to another aspect of the invention, there is provided a method of detecting *Strongyloides* in a biological sample, comprising the steps of:

a) providing at least one biological sample;

b) contacting the at least one biological sample with an antigen, wherein the antigen is an isolated or recombinant *Strongyloides stercoralis* protein, comprising the amino acid sequence shown in SEQ ID NO: 2 or SEQ ID NO: 4 or antigenic fragment thereof; and c) detecting specific and selective antigen-antibody binding, wherein the binding indicates the presence of *Strongyloides stercoralis*-specific antibodies present in the biological sample.

In a preferred embodiment of the method of the invention, the antigen-antibody binding is detected using immunoassay. The immunoassay may include various formats, for example chip-based immunoassay, ELISA, Western blot, flow-through (vertical flow) test or lateral flow assay. More preferably, the detection method may be a flow-through (vertical flow) test or lateral flow dot dipstick test, because these methods advantageously do not require sophisticated machinery to perform in a point of care scenario.

According to another aspect of the invention, there is provided a method of detecting *Strongyloides* in a biological sample, comprising the steps of:

a) providing at least one biological sample;

b) detecting the presence of *Strongyloides* protein in the biological sample, wherein the detection of the *Strongyloides* protein comprising the amino acid sequence shown in SEQ ID NO: 2 or SEQ ID NO: 4 or fragment thereof in the biological sample constitutes detection of *Strongyloides*.

In another preferred embodiment of the method of the invention, the *Strongyloides* protein is detected with an antibody that specifically and selectively binds the protein.

In another preferred embodiment of the method of the invention, the *Strongyloides* protein is detected using immunoassay.

According to another aspect of the invention, there is provided a method of detecting whether a subject has strongyloidiasis, comprising the steps;

a) contacting a test sample from the subject with an antigen, wherein the antigen is an isolated or recombinant *Strongyloides* protein or a fragment thereof, and detecting specific and selective antibody-antigen binding, wherein the binding indicates the presence of strongyloidiasis in the subject; or b) detecting the presence of *Strongyloides* protein in a test sample from the subject, wherein the detection of the *Strongyloides* protein in the test sample indicates the presence of strongyloidiasis.

In another preferred embodiment of the method of the invention, the *Strongyloides* protein or fragment or variant thereof is encoded by an isolated or recombinant nucleic acid molecule comprising the nucleic acid sequence shown in SEQ ID NO: 1 or SEQ ID NO: 3 or a fragment thereof.

In another preferred embodiment of the method of the invention, the *Strongyloides* specific antibodies are IgG antibodies.

According to another aspect of the invention, there is provided a vaccine comprising at least one *Strongyloides* protein or antigenic fragment or variant thereof. In a preferred embodiment, the vaccine comprises at least one protein or antigenic fragment or variant selected from SEQ ID NO: 2 and SEQ ID NO: 4 which may be used separately or in combination.

According to another aspect of the invention, there is provided a method of treatment or prophylaxis of strongyloidiasis, comprising administering to a subject an efficacious amount of a vaccine as defined above.

According to another aspect of the invention, there is provided a use of at least one *Strongyloides* protein or antigenic fragment or variant thereof for the preparation of a vaccine for the prophylaxis or treatment of strongyloidiasis.

According to another aspect of the invention, there is provided an expression construct comprising a nucleic acid comprising the sequence shown in SEQ ID NO: 1 or SEQ ID NO: 3 or antigen encoding fragment thereof.

According to another aspect of the invention, there is provided a kit for screening a biological sample for the presence of *Strongyloides*-specific antibody and/or *Strongyloides* antigen, comprising:

a) an isolated or recombinant *Strongyloides* protein, or a fragment thereof according to any aspect of the invention, capable of binding to *Strongyloides*-specific antibody present in the biological sample; and/or b) an isolated or recombinant *Strongyloides* protein-specific antibody according to any aspect of the invention, capable of binding to *Strongyloides* protein present in the biological sample.

In a preferred embodiment, the kit further comprises immunoassay reagents when a) or b) are present.

In another preferred embodiment, the kit further comprises a flow-through (vertical flow) test device or lateral flow assay device to detect the presence of *Strongyloides* antibodies, protein or nucleic acid. Preferably the device may include a flow-through membrane or lateral flow dipstick dot test strip.

A method of treatment or prophylaxis of strongyloidiasis, comprising administering to a subject an efficacious amount of an isolated or recombinant *Strongyloides* protein comprising the amino acid sequence shown in SEQ ID NO: 2 or SEQ ID NO: 4 or an immunogenic fragment or variant thereof.

EXAMPLES

A person skilled in the art will appreciate that the present invention may be practiced without undue experimentation according to the methods given herein. The methods, techniques and chemicals are as described in the references given or from protocols in standard biotechnology and molecular biology text books such as Sambrook and Russell, Molecular Cloning: A Laboratory Manual, Cold Springs Harbor Laboratory, New York (2001).

Example 1: Screening for L3 Stage Larvae Antigens

Immunoscreening of *S. stercoralis* cDNA library was performed to identify cDNA clones representing specific genes expressed in the L3 larvae stage that produce antigenic recombinant proteins that would specifically be recognized by immunoglobulin antibodies i.e. $IgG_4$ and IgG present in a biological sample. This study has led to the identification of two cDNA clones, designated SsIa and Ss3a.

The diagnostic sensitivity and specificity of the isolated SsIa and Ss3a phage clones was evaluated in an immunoblotting study utilizing a panel of serum samples from patients with strongyloidiasis, healthy individuals or patients infected with other diseases (FIG. 1). Both of the cDNA clones produced recombinant proteins (rSs1a and rSs3a) which demonstrated high diagnostic sensitivity and specificity in detecting anti-*Strongyloides* antibodies in human serum samples (Table 1).

TABLE 1

Summary of the reactivity of phage immunoblot using rSsIa and rSs3a

| Serum samples | Number of serum samples | | | | | |
|---|---|---|---|---|---|---|
| | rSsIa | | | rSs3a | | |
| | Positive | Negative | Total | Positive | Negative | Total |
| Positive | 14 (100%) | 3 | 17 | 12 (100%) | 3 | 15 |
| Negative | 0 | 19 (86.4%) | 19 | 0 | 27 (90%) | 27 |
| Total | 14 | 22 | 36 | 12 | 30 | 42 |

Diagnostic sensitivity of rSs1a: 100%
Diagnostic specificity of rSs1a: 86.4%
Diagnostic sensitivity of rSs3a: 100%
Diagnostic specificity of rSs3a: 90%

These clones were then in vivo excised to convert the phagemids into plasmids, followed by plasmid extraction and sequencing, to determine the DNA sequences.

The 894 nucleotide sequence of the insert of the phage clone SsIa of *Strongyloides stercoralis* L3 larvae stage is represented by SEQ ID NO: 1 (FIG. 2A). The nucleotides encoding the predicted protein sequence are underlined. The predicted 297 amino acid sequence encoded by the insert of the phage clone Ss1a of *Strongyloides stercoralis* L3 larvae stage is represented by SEQ ID NO: 2 (FIG. 2B).

The 818 nucleotide sequence of the insert of the phage clone Ss3a of *Strongyloides stercoralis* L3 larvae stage is represented by SEQ ID NO: 3 (FIG. 3A). The nucleotides encoding the predicted protein sequence are underlined. The predicted 224 amino acid sequence encoded by the insert of the phage clone Ss3a of *Strongyloides stercoralis* L3 larvae stage is represented by SEQ ID NO: 4 (FIG. 3B).

Bioinformatics analysis of the deduced nucleotide sequence of the DNA insert of SsIa revealed that it has 99% identity to the *Strongyloides stercoralis* genome assembly S_stercoralis_PV0001, scaffold SSTP_contig0000018 with accession number LL999076.1, where Ss1a is represented by nucleotides 296-894 of SEQ ID NO: 1 (FIG. 4). Analysis of the translated protein of the SsIa cDNA (SEQ ID NO: 2) using Blastp showed the highest similarity to *Strongyloides ratti* immunoglobulin-binding protein 1 [Identities=188/247 (76%), Positives=225/247 (91%), Gaps=1/247 (0%)] with accession number CEF66010.1 (FIG. 5). Alignment to *Strongyloides ratti* may be due to the fact that the genome sequencing and annotation of *Strongyloides stercoralis* has not been completed.

The nucleotide sequence of the phage cDNA clone Ss3a showed the highest identity to *Strongyloides stercoralis* genome assembly S_stercoralis_PV0001, scaffold SSTP_scaffold0000002 with accession number LL999049.1 [Identities=818/819 (99%), Gaps=0/819 (0%)], where Ss3a is represented by nucleotides 1-818 of SEQ ID NO: 3 (FIG. 6). There is a difference (substitution of T/A) at position 759. Blastp searches demonstrated a high percent of similarity (67% identity; 76% homology) of the Ss3a translated protein sequence (SEQ ID NO: 4) to a hypothetical protein SRAE_2000383300 from *Strongyloides ratti* with accession number CEF69183.1 (FIG. 7). There is one gap introduced into the clone sequence at amino acid position 218 to maximise alignment.

The SsIa DNA sequence insert of the plasmid was codon optimized for *E. coli* expression by EPOCH Life Science Inc. (Texas, USA) and custom-cloned into the expression vector pET28b (Novagen, Madison, Wis., USA), followed by transformation into BL21(DE3) host cells (Novagen, Madison, Wis., USA). Expression of the plasmid in Terrific Broth (900 ml $H_2O$ containing 12 g Tryptone, 24 g Yeast extract, 4 ml Glycerol sterilised plus 100 ml solution of 0.17M KH2PO4 and 0.72M K2HPO4) yielded a significant amount of soluble His-tagged rSsIa protein with an observed molecular weight of 37 kDa (FIG. 8A). The evidence of expression of the SsIa-His fusion protein was verified by Western blot analysis using anti-His HRP antibody and validated by MALDI-TOF/TOF analysis.

Meanwhile, the codon-optimized Ss3a cDNA clone was custom-cloned into a pET42a vector (Novagen, Madison, Wis., USA) and transformed into Lemo21(DE3) cells (New England Biolabs, Hitchin, UK), producing a GST-fusion protein designated rSs3a (FIG. 8B). Western blot analysis of the expressed fusion protein using anti-GST HRP antibody determined the molecular weight to be about 45 kDa, which was validated by MALDI TOF/TOF analysis.

Western blot analyses of both recombinant proteins, rSs1a and rSs3a, demonstrated a high diagnostic sensitivity and specificity in detecting anti-*Strongyloides* $IgG_4$ in human serum samples (FIG. 9, Table 2), prompting further evaluation of both recombinant proteins for application in the development of a lateral flow dot dipstick (LFA) test.

TABLE 2

Summary of the diagnostic sensitivity and specificity of a) rSsIa and b) rSs3a by Western blot analysis.

| Serum samples | Number of serum samples | | | | | |
|---|---|---|---|---|---|---|
| | rSsIa | | | rSs3a | | |
| | Positive | Negative | Total | Positive | Negative | Total |
| Positive | 11 (100%) | 2 | 13 | 21 (100%) | 4 | 25 |
| Negative | 0 | 8 (80%) | 8 | 0 | 87 (95.6%) | 87 |
| Total | 11 | 10 | 21 | 21 | 91 | 112 |

Diagnostic sensitivity of rSsIa: 100%
Diagnostic specificity of rSsIa: 80%
Diagnostic sensitivity of rSs3a: 100%
Diagnostic specificity of rSs3a: 95.6%

In developing the lateral flow dot dipstick test for rSsIa, anti-human IgG$_4$ conjugated to colloidal gold was used as the conjugate reagent whereas for rSs3a anti-GST conjugated to colloidal gold was used as the conjugate reagent. This was due to the large GST tag fused to the rSs3a protein that was not removed. Both lateral flow strips were then tested with a panel of serum samples obtained from *Strongyloides*-infected patients and controls (FIG. 10A-B). Results of the evaluation studies showed that both lateral flow dot dipstick tests were highly sensitive and specific in detecting anti-*Strongyloides* IgG$_4$ antibody in serum samples of *Strongyloides*-infected humans (Table 3).

TABLE 3

Summary of the diagnostic sensitivity and specificity of dipstick dot tests using a) rSsIa and b) rSs3a.

| Serum samples | Number of serum samples | | | | | |
|---|---|---|---|---|---|---|
| | rSsIa | | | rSs3a | | |
| | Positive | Negative | Total | Positive | Negative | Total |
| Positive | 27 (90%) | 1 | 28 | 10 (100%) | 0 | 10 |
| Negative | 3 | 45 (98%) | 48 | 0 | 10 (100%) | 10 |
| Total | 30 | 46 | 76 | 10 | 10 | 20 |

Diagnostic sensitivity of rSsIa: 90%
Diagnostic specificity of rSsIa: 98%
Diagnostic sensitivity of rSs3a: 100%
Diagnostic specificity of rSs3a: 100%

Further work will be performed to produce rSs3a using a suitable His-tagged vector that can yield soluble recombinant protein with good yield and purity.

We have successfully produced two *Strongyloides* recombinant proteins, rSsIa and rSs3a, which show high sensitivity and specificity in detecting anti-*Strongyloides* antibody in the serum of human subjects using western blot and lateral flow dipstick dot tests. The development of a lateral flow test to detect strongyloidiasis is important since this test format is very suitable for use in resource-poor settings where the disease is endemic.

REFERENCES

1. Anderson, N W, Klein, D M, Dornink, S M, Jespersen, D J, Kubofcik, J, Nutman, T B, Merrigan, S D, Couturier, M R & Theel, E S (2014) Comparison of three immunoassays for detection of antibodies to *Strongyloides stercoralis*. Clin. Vaccine Immunol., 21, 732-736.
2. Muennig, P, Pallin, D, Sell, R & Chan, M (1999) The cost effectiveness of strategies for treatment of intestinal parasites in immigrants. N Engl J Med, 340: 773-779.
3. Olsen, A, van Lieshout, L, Marti, H, Polderman, T, Polman, K, Steinmann, P, Stothard, R, Thybo, S, Verweij, J J & Magnussen, P (2009) Strongyloidiasis the most neglected of the neglected tropical diseases? Trans. R. Soc. Trop. Med. Hyg., 103, 967-972.
4. Ramanathan, R, Burbelo, P D, Groot, S, Iadarola, M J, Neva, F A & Nutman, T B (2008) A luciferase immunoprecipitation systems assay enhances the sensitivity and specificity of diagnosis of *Strongyloides stercoralis* infection. The Journal of Infectious Diseases, 198, 44-451.
5. Ravi, V, Ramachandran, S, Thompson, R W, Andersen, J F & Neva, F A (2002) Characterization of a recombinant immunodiagnostic antigen (NIE) from *Strongyloides stercoralis* L3-stage larvae. Mol. Biochem. Parasitol., 125, 73-81.
6. Requena-Mendez, A, Buonfrate, D, Bisoffi, Z & Guti¶irrez, J (2014) Advances in the Diagnosis of Human Strongyloidiasis. Curr Trop Med Rep, 1, 207-215.
7. Requena-M¶ndez, A, Chiodini, P, Bisoffi, Z, Buonfrate, D, Gotuzzo, E & Mu¿oz, J (2013) The laboratory diagnosis and follow up of strongyloidiasis: a systematic review. PLoS Negl. Trop. Dis., 7, e2002.
8. Siddiqui, A A & Berk, S L (2001) Diagnosis of *Strongyloides stercoralis* infection. Travel Medicine, 33, 1040-1047.

The invention claimed is:

1. A method of detecting *Strongyloides* in a biological sample, comprising the steps of: a) contacting the biological sample with an antigen, wherein the antigen is an isolated or recombinant *Strongyloides stercoralis* protein selected from the group comprising the amino acid sequence shown in SEQ ID NO: 2 or SEQ ID NO: 4; and b) detecting specific and selective antigen-antibody binding, wherein binding indicates the presence of *Strongyloides stercoralis*-specific antibodies present in the biological sample.

2. The method according to claim 1, wherein the antigen-antibody binding is detected using immunoassay.

3. The method according to claim 2, wherein the immunoassay is Western blot, flow-through (vertical flow) test or lateral flow assay.

4. A *Strongyloides* screening kit to screen an isolated biological sample for the presence of *Strongyloides*-specific antibody comprising: a) an isolated or recombinant *Strongyloides* protein comprising the amino acid sequence shown in SEQ ID NO: 2 or SEQ ID NO: 4 capable of binding to *Strongyloides*-specific antibody present in the biological sample.

5. The kit according to claim 4, further comprising immunoassay reagents.

6. The kit according to claim 4, further comprising a lateral flow assay device to detect the presence of *Strongyloides* antibodies or protein.

* * * * *

SEQUENCE LISTING

<160> NUMBER OF SEQ ID NOS: 4

<210> SEQ ID NO 1
<211> LENGTH: 894
<212> TYPE: DNA
<213> ORGANISM: Strongyloides stercoralis

<400> SEQUENCE: 1

```
atggaggaca cagataattt aagtgttaag gatatctttc aaaagtatag aaatttaatc      60
cttaaagggg atggtaattt ttctgataaa caggaaatcc tagaaaagtc tattatagaa     120
atgaaaaaat taaaagataa ctttgatttg ggagatatta tatcattaaa tgaccaaata     180
```

```
gatgaaatat ctccatctga tcttgagatg ttccttctac catacttaat agggacagct    240
tattataatg ttaaagctac ggatcctaaa aaaaggatgg atgtattgtt gaatgttaag    300
atttatatgc aagagtatct tgaaaattta cacctctatt atatcattga ttttgtctta    360
ccatggctta agataaaga agagtcatct agtgggcctt ctatatcaaa agatgacaaa    420
ttaactccat ccgaaggag ggaaagaata cttaaaagac atcaaatgta taaaaatttt    480
gaagaaaagt tgttggagta tgaaaatgaa gcctcaacgg ctggtggttt ggatgatata    540
acacaaagaa attatgtcct agcaaagtta agaacttatg ctcttaaggc aatgatggat    600
ctcgagaaga ttggggagga acttggcata ttagagtata tgttaaaaat aaaacaaggt    660
gaagttgttg aggagaaaca taaacctcca ccaaaaatga caacttatcg tattgtaagg    720
aatgaggaac aaaaaagtc tttggaatgg gttataaaa tattccaaca cttactgtgg    780
atgagtggta tcgtgaaatg gatacaaaag gacattttaa tattaaacag gacgccggag    840
cacagcccaa tacctcaaat aatggaggag acgatgatga tgatgataat ttag          894
```

```
<210> SEQ ID NO 2
<211> LENGTH: 297
<212> TYPE: PRT
<213> ORGANISM: Strongyloides stercoralis

<400> SEQUENCE: 2

Met Glu Asp Thr Asp Asn Leu Ser Val Lys Asp Ile Phe Gln Lys Tyr
1               5                   10                  15

Arg Asn Leu Ile Leu Lys Gly Asp Gly Asn Phe Ser Asp Lys Gln Glu
            20                  25                  30

Ile Leu Glu Lys Ser Ile Ile Glu Met Lys Lys Leu Lys Asp Asn Phe
        35                  40                  45

Asp Leu Gly Asp Ile Ile Ser Leu Asn Asp Gln Ile Asp Glu Ile Ser
    50                  55                  60

Pro Ser Asp Leu Glu Met Phe Leu Leu Pro Tyr Leu Ile Gly Thr Ala
65                  70                  75                  80

Tyr Tyr Asn Val Lys Ala Thr Asp Pro Lys Lys Arg Met Asp Val Leu
                85                  90                  95

Leu Asn Val Lys Ile Tyr Met Gln Glu Tyr Leu Glu Asn Leu His Leu
            100                 105                 110

Tyr Tyr Ile Ile Asp Phe Val Leu Pro Trp Leu Lys Asp Lys Glu Glu
        115                 120                 125

Ser Ser Ser Gly Pro Ser Ile Ser Lys Asp Asp Lys Leu Thr Pro Ser
    130                 135                 140

Glu Arg Arg Glu Arg Ile Leu Lys Arg His Gln Met Tyr Lys Asn Phe
145                 150                 155                 160

Glu Glu Lys Leu Leu Glu Tyr Glu Asn Glu Ala Ser Thr Ala Gly Gly
                165                 170                 175

Leu Asp Asp Ile Thr Gln Arg Asn Tyr Val Leu Ala Lys Leu Arg Thr
            180                 185                 190

Tyr Ala Leu Lys Ala Met Met Asp Leu Glu Lys Ile Gly Glu Glu Leu
        195                 200                 205

Gly Ile Leu Glu Tyr Met Leu Lys Ile Lys Gln Gly Glu Val Val Glu
    210                 215                 220

Glu Lys His Lys Pro Pro Lys Met Thr Thr Tyr Arg Ile Val Arg
225                 230                 235                 240

Asn Glu Glu Gln Lys Lys Ser Leu Glu Trp Val Ile Lys Ile Phe Gln
```

```
                    245                 250                 255
His Leu Leu Trp Met Ser Gly Ile Val Lys Trp Ile Gln Lys Asp Ile
            260                 265                 270

Leu Ile Leu Asn Arg Thr Pro Glu His Ser Pro Ile Pro Gln Ile Met
            275                 280                 285

Glu Glu Thr Met Met Met Ile Ile
            290                 295

<210> SEQ ID NO 3
<211> LENGTH: 818
<212> TYPE: DNA
<213> ORGANISM: Strongyloides stercoralis

<400> SEQUENCE: 3
atatttctat atacttctca gctgaagtgt aattgttttt cagttttcct actaacaatt      60
cacccaccaa ctaaccagtt tccactctaa tcttctaatg atgaatcgtt ctattctttt     120
ggtgctcttt gtttcattaa ttgctatggt ttcttgcaag agtctagcct cctactctga     180
taacggacca ctaggttcta tgttaagagc cgatgaatct actgacagtc ttggtgatgc     240
agtatctggt tctaccacct ctacaacaac acaagctcct tctactacca cttcagagtc     300
tttggaatct acttcgactt ctagtagttc ctcagaaaat ccaccttcag gtgccacggc     360
agctgccgct actatggata ttacttctac taccgccccc gacgagacta ctactaccac     420
agctccagcc gttgccactg aaactactac tactactact cctgctgtta caactacaac     480
agcaccaact gaagcaccaa ctcctgtcag taaggaagct accacaaccg aatcttcctc     540
tccagcaggt caggatgttt cctcaaccac agtcgagtca tcatcctccg ttccagagag     600
gagatcaaca tccagtgaac cctcagaaac gacaacatca ccaggagaaa tttcaacatc     660
tactggagct ggtaacacaa caacacctga accttctgct ggaagtgtta atggtgttca     720
atttaaagct atattgattt ctattatatc attatttgta ttttaatttt gattgtagat     780
aatatatgtg aaggataat ttactatttt aaataaaa                              818

<210> SEQ ID NO 4
<211> LENGTH: 224
<212> TYPE: PRT
<213> ORGANISM: Strongyloides stercoralis

<400> SEQUENCE: 4

Met Met Asn Arg Ser Ile Leu Leu Val Leu Phe Val Ser Leu Ile Ala
1               5                   10                  15

Met Val Ser Cys Lys Ser Leu Ala Ser Tyr Ser Asp Asn Gly Pro Leu
            20                  25                  30

Gly Ser Met Leu Arg Ala Asp Glu Ser Thr Asp Ser Leu Gly Asp Ala
        35                  40                  45

Val Ser Gly Ser Thr Thr Ser Thr Thr Thr Gln Ala Pro Ser Thr Thr
    50                  55                  60

Thr Ser Glu Ser Leu Glu Ser Thr Ser Thr Ser Ser Ser Ser Ser Glu
65                  70                  75                  80

Asn Pro Pro Ser Gly Ala Thr Ala Ala Ala Thr Met Asp Ile Thr
            85                  90                  95

Ser Thr Thr Ala Pro Asp Glu Thr Thr Thr Thr Ala Pro Ala Val
            100                 105                 110

Ala Thr Glu Thr Thr Thr Thr Thr Pro Ala Val Thr Thr Thr
            115                 120                 125
```

```
Ala Pro Thr Glu Ala Pro Thr Pro Val Ser Lys Glu Ala Thr Thr Thr
    130             135             140

Glu Ser Ser Ser Pro Ala Gly Gln Asp Val Ser Ser Thr Thr Val Glu
145             150             155             160

Ser Ser Ser Ser Val Pro Glu Arg Arg Ser Thr Ser Ser Glu Pro Ser
            165             170             175

Glu Thr Thr Ser Pro Gly Glu Ile Ser Thr Ser Thr Gly Ala Gly
        180             185             190

Asn Thr Thr Thr Pro Glu Pro Ser Ala Gly Ser Val Asn Gly Val Gln
        195             200             205

Phe Lys Ala Ile Leu Ile Ser Ile Ile Ser Leu Phe Val Phe Leu Ile
    210             215             220
```